US012114967B2

United States Patent
Ajala et al.

(10) Patent No.: US 12,114,967 B2
(45) Date of Patent: Oct. 15, 2024

(54) SYSTEMS AND METHODS OF CORRECTING EFFECTS OF HIGH-ORDER CONCOMITANT FIELDS IN THREE-DIMENSIONAL MAGNETIC RESONANCE IMAGING

(71) Applicant: GE PRECISION HEALTHCARE LLC, Wauwatosa, WI (US)

(72) Inventors: Afis Ajala, Schenectady, NY (US);
Seung-Kyun Lee, Cohoes, NY (US);
Thomas Kwok-Fah Foo, Clifton Park, NY (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 136 days.

(21) Appl. No.: 18/156,161

(22) Filed: Jan. 18, 2023

(65) Prior Publication Data
US 2024/0237911 A1 Jul. 18, 2024

(51) Int. Cl.
*A61B 5/055* (2006.01)
*G01R 33/385* (2006.01)
(Continued)

(52) U.S. Cl.
CPC ............ *A61B 5/055* (2013.01); *G01R 33/385* (2013.01); *G01R 33/56581* (2013.01); *G01R 33/4824* (2013.01)

(58) Field of Classification Search
CPC .................. A61B 5/055; G01R 33/385; G01R 33/56581; G01R 33/4824
See application file for complete search history.

(56) References Cited

U.S. PATENT DOCUMENTS

| 10,613,174 B2 | 4/2020 | Bhat |
| 10,712,420 B2 | 7/2020 | Shengzhen et al. |

(Continued)

FOREIGN PATENT DOCUMENTS

| EP | 3304098 A1 | 4/2018 |
| WO | 2016180983 A1 | 11/2016 |
| WO | 2016196103 A1 | 12/2016 |

OTHER PUBLICATIONS

Abad et al,. "Brain Microstructure Imaging with Ultrahigh B-Encoding using MAGNUS High Performance Gradients", in ISMRM 2022 Annual Proceedings (2022).
(Continued)

*Primary Examiner* — G.M. A Hyder
(74) *Attorney, Agent, or Firm* — Armstrong Teasdale LLP

(57) ABSTRACT

A magnetic resonance (MR) system is provided. The MR system includes a gradient coil assembly and a concomitant field correction computing device. The at least one processor of the computing device is programmed to receive MR signals acquired with the MR system using a three-dimensional (3D) pulse sequence, wherein a kx dimension and a ky dimension in k-space are sampled along non-Cartesian trajectories. The at least one processor is further programmed to correct effects of concomitant fields generated by gradient fields applied by the gradient coil assembly by adjusting the MR signals with second-order concomitant phases accumulated from second-order concomitant fields, and reconstructing MR images based on the adjusted MR signals. The second-order concomitant phases vary as functions of time and spatial locations. The at least one processor is also programmed to output the MR images.

19 Claims, 8 Drawing Sheets
(2 of 8 Drawing Sheet(s) Filed in Color)

(51) Int. Cl.
  *G01R 33/565* (2006.01)
  *G01R 33/48* (2006.01)

(56) References Cited

U.S. PATENT DOCUMENTS

| | | | | |
|---|---|---|---|---|
| 11,243,287 | B2* | 2/2022 | Harris | G01R 33/3875 |
| 11,294,016 | B1 | 4/2022 | Foo | |
| 2018/0203088 | A1* | 7/2018 | Tao | G01R 33/56563 |
| 2021/0166447 | A1 | 6/2021 | Koerzdoerfer | |
| 2023/0095599 | A1* | 3/2023 | Roberts | G01R 33/5608 |
| | | | | 324/309 |

OTHER PUBLICATIONS

Abad et al., Calibration of concomitant field offsets using phase-contrast MRI for asymmetric gradient coils, Magn Reson Med. Jan. 2023;89(1):262-275. doi: 10.1002/mrm.29452. Epub Sep. 21, 2022.
Ajala et al., "3D Pseudo-Continuous Arterial Spin Labeling Acquisition using a High-Performance Gradient System: A Scan Time and Image Quality Assessment", in ISMRM 2022 Annual Proceedings (2022).
Bernstein et al., "Concomitant Gradient Terms in Phase Contrast MR: Analysis and Correction", MRM 39:300-308 (1998).
Du et al., "Correction of Concomitant Magnetic Field-Induced Image Artifacts in Nonaxial Echo-Planar Imaging" MRM 48:509-515 (2002), DOI: 10.1002/mrm.10249.
Foo et al., "Highly efficient head-only magnetic field insert gradient coil for achieving simultaneous high gradient amplitude and slew rate at 3.0T (MAGNUS) for brain microstructure imaging", Magnetic Resonance in Medicine 83, 2356-2369 (2019).
King et al, "Concomitant Gradient Field Effects in Spiral Scans", MRM 41:103-112 (1999).
Setsompop et al., "Pushing the limits of in vivo diffusion MRI for the Human Connectome Project", Neuroimage 80, 220-233 (2013).
Shih et al,. "Initial Clinical Experience with MAGNUS Ultra-High-Performance Gradient Coil for Diffusion Microstructure Imaging of Intracranial Pathology", in ISMRM 2022 Annual Proceedings (2022).

Tao et al,. "The Effect of Concomitant Fields in Fast Spin Echo Acquisition on Asymmetric MRI Gradient Systems" Magn Reson Med 79, 1354-1364 (2018).
Tao et al., "Gradient Pre-Emphasis to Counteract First-Order Concomitant Fields on Asymmetric MRI Gradient Systems", MRM 77:2250-2262 (2017), published online Jul. 4, 2016, DOI: 10.1002/mrmt.26315.
Weavers et al., "B0 Concomitant Field Compensation for MRI Systems Employing Asymmetric Transverse Gradient Coils", MRM 79:1538-1544 (2018), published online Jun. 21, 2017, DOI: 10.1002/mrm.26790.
Weiger et al,. "A high-performance gradient insert for rapid and short-T2 imaging at full duty cycle", Magn Reson Med 79, 3256-3266 (2018).
Wilm et al., Single-Shot Spiral Imaging Enabled by an Expanded Encoding Model: Demonstration in Diffusion MRI, MRM, 77:83-91, published onine Oct. 21, 2016, DOI: 10.1002/mrm.26493.
Yudilevich et al., "Interpolation from Samples on a Linear Spiral Scan", IEEE Trans Med Imaging, 1987;6(3):193-200, doi: 10.1109/TMI.1987.4307827.
Zhou et al., "Artifacts Induced by Concomitant Magnetic Field in Fast Spin-Echo Imaging", MRM 40:582-591 (1998).
Zhu et al., "Characterizing Restricted Diffusion in Pre-/Post- treatment Gliomas Using Time-dependent Diffusion MRI at Ultra-high-gradient Human 3.0T", in ISMRM 2022 Annual Proceedings (2022).
Niu C. et al., "A Novel Active Shim Coil Design Scheme for the Effective Imaging Region above the Patient Bed in MRI", J Supercond Nov Magn 35, 1685-1691 (2022). https://doi.org/10.1007/s10948-022-06249-x.
Christoph Juchem et al., "Dynamic multi-coil shimming of the human brain at 7T", Journal of Magnetic Resonance, vol. 212, Issue 2, 2011, pp. 280-288, ISSN 1090-7807, https://doi.org/10.1016/j.jmr.2011.07.005.
Liao et al., "Flexible use of AC/DC shim array for eddy-currents and concomitant fields mitigation with demonstrated applications in diffusion-prepared acquisition and non-Cartesian sampling", in ISMRM 2023 Workshop on Data Sampling & Image Reconstruction, published Jan. 3, 2023.

* cited by examiner

SYSTEMS AND METHODS OF CORRECTING EFFECTS OF HIGH-ORDER CONCOMITANT FIELDS IN THREE-DIMENSIONAL MAGNETIC RESONANCE IMAGING

BACKGROUND

The field of the disclosure relates generally to systems and methods of medical imaging, and more particularly, to systems and methods of correcting effects of high-order concomitant fields in a three-dimensional (3D) magnetic resonance (MR) imaging.

Magnetic resonance imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

Concomitant fields generated by gradients in an MR system introduce errors in the MR signals and therefore may interfere with diagnosis. Known methods are disadvantaged in some aspects and improvements are desired.

BRIEF DESCRIPTION

In one aspect, a magnetic resonance (MR) system is provided. The MR system includes a gradient coil assembly including an x gradient coil, a y gradient coil, and a z gradient coil. The x gradient coil, the y gradient coil, or the z gradient coil is configured to apply a gradient field along an x direction (Gx), a gradient field along a y direction (Gy), or a gradient field along a z direction (Gz), respectively. The MR system also includes a concomitant field correction computing device, including at least one processor in communication with at least one memory device. The at least one processor is programmed to receive MR signals acquired with the MR system using a three-dimensional (3D) pulse sequence, wherein a kx dimension and a ky dimension in k-space are sampled along non-Cartesian trajectories. The at least one processor is further programmed to correct effects of concomitant fields generated by gradient fields applied by the gradient coil assembly by adjusting the MR signals with second-order concomitant phases accumulated from second-order concomitant fields, and reconstructing MR images based on the adjusted MR signals. The second-order concomitant phases vary as functions of time and spatial locations. The at least one processor is also programmed to output the MR images.

In another aspect, a concomitant field correction computing device for correcting effects of concomitant fields in an MR system is provided. The concomitant field correction computing device includes at least one processor in communication with at least one memory device. The at least one processor is programmed to receive MR signals acquired with an MR system using a 3D pulse sequence. The MR system includes a gradient coil assembly including an x gradient coil, a y gradient coil, and a z gradient coil. The x gradient coil, the y gradient coil, or the z gradient coil is configured to apply a gradient field along an x direction (Gx), a gradient field along a y direction (Gy), or a gradient field along a z direction (Gz), respectively. The at least one processor is further programmed to correct effects of concomitant fields generated by gradient fields applied by the gradient coil assembly by adjusting the MR signals with second-order concomitant phases accumulated from second-order concomitant fields, and reconstructing MR images based on the adjusted MR signals. The second-order concomitant phases vary as functions of time and spatial locations, The at least one processor is also programmed to output the MR images.

In one more aspect, a method for correcting effects of concomitant fields in an MR system is provided. The method includes receiving MR signals acquired with an MR system using a 3D pulse sequence. The MR system includes a gradient coil assembly including an x gradient coil, a y gradient coil, and a z gradient coil. The x gradient coil, the y gradient coil, or the z gradient coil is configured to apply a gradient field along an x direction (Gx), a gradient field along a y direction (Gy), or a gradient field along a z direction (Gz), respectively. The method further includes correcting effects of concomitant fields generated by gradient fields applied by the gradient coil assembly by adjusting the MR signals with high-order concomitant phases accumulated from high-order concomitant fields, and reconstructing MR images based on the adjusted MR signals. The high-order concomitant phases vary as functions of time and spatial locations, and a high order is a second order or higher. The method also includes outputting the MR images.

DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
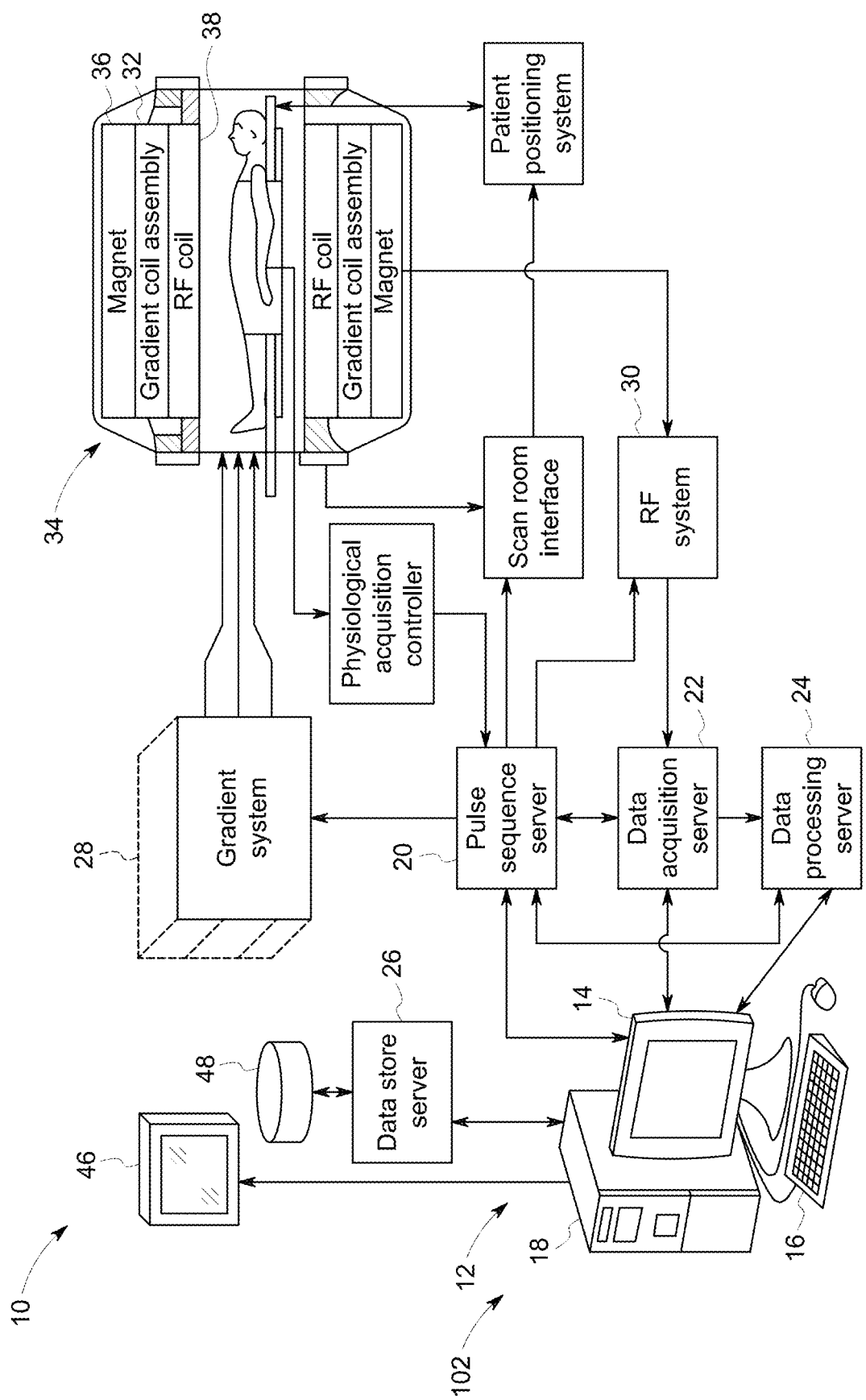
FIG. 1 is a schematic diagram of an example magnetic resonance (MR) system.

The disclosure includes systems and methods of correcting effects of concomitant fields in three-dimensional (3D) magnetic resonance (MR) imaging. Concomitant fields introduce errors to MR signals and cause artifacts such as pixel shifts, in-plane blurring, and/or through-plane blurring in MR images of a subject. As used herein, a subject is a human, an animal, or a phantom, or part of a human, an animal, or a phantom, such as an organ or tissue. 3D Non-Cartesian sampling in one or more dimensions in the k-space is used as examples for illustration purposes. Systems and methods described herein may be applied to MR signals acquired with any 3D pulse sequence including a 3D pulse sequence with Cartesian sampling to correct high-order concomitant phase error. As used herein, the order in a high-order concomitant field term refers to spatial variation of the concomitant field term, and an order is the order of the function of the concomitant field with respect to the spatial location x, y, or z. For example, if a concomitant field term is a function of $x^2$, the concomitant field term is a second-order concomitant field term. The second-order concomitant phase error is described as examples for illustration purposes only. Systems and methods described herein may be applied to correct concomitant phase errors of third order or higher by including phase errors from concomitant fields of third order or higher. Third and higher-ordered concomitant field errors may be in issue at low field strengths and high maximum gradient amplitudes such as systems having a field strength less than 1.5 T and/or having gradient amplitudes greater than 400 mT/m. An MR system is described herein as an example for illustration purposes only. Systems and methods described herein may be applied to other image modalities such as PET-MR (positron emission tomography-magnetic resonance) systems. Method aspects will be in part apparent and in part explicitly discussed in the following description.

In magnetic resonance imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as $B_0$ and extends in the longitudinal or z direction. In acquiring an MRI image, a magnetic field (referred to as an excitation field $B_1$), which is in the x-y plane and near the Larmor frequency, is generated by a radiofrequency (RF) coil and may be used to rotate, or "tip," the net magnetic moment Mz of the nuclei from the z direction to the transverse or x-y plane. A signal, which is referred to as an MR signal, is emitted by the nuclei, after the excitation signal $B_1$ is terminated. To use the MR signals to generate an image of a subject, magnetic field gradient pulses (Gx, Gy, and Gz) are used. The gradient pulses are used to scan through the k-space, the space of spatial frequencies or inverse of distances. A Fourier relationship exists between the acquired MR signals and an image of the subject, and therefore the image of the subject can be derived by Fourier transform of the MR signals.

FIG. 1 illustrates a schematic diagram of an example MRI system 10. In the example embodiment, MRI system 10 includes a workstation 12 having a display 14 and a keyboard 16. Workstation 12 includes a processor 18, such as a commercially available programmable machine running a commercially available operating system. Workstation 12 provides an operator interface that allows scan prescriptions to be entered into MRI system 10. Workstation 12 is coupled to a pulse sequence server 20, a data acquisition server 22, a data processing server 24, and a data store server 26. Workstation 12 and each server 20, 22, 24, and 26 communicate with each other.

In the example embodiment, pulse sequence server 20 responds to instructions downloaded from workstation 12 to operate a gradient system 28 and a radiofrequency ("RF") system 30. The instructions are used to produce gradient and RF waveforms in MR pulse sequences. An RF coil 38 and a gradient coil assembly 32 are used to perform the prescribed MR pulse sequence. RF coil 38 is shown as a whole body RF coil. RF coil 38 may also be a local coil that may be placed in proximity to the anatomy to be imaged, or a coil array that includes a plurality of coils.

In the example embodiment, gradient waveforms used to perform the prescribed scan are produced and applied to gradient system 28, which excites gradient coils in gradient coil assembly 32 to produce the magnetic field gradients $G_x$, $G_y$, and $G_z$ used for position-encoding MR signals. Gradient coil assembly 32 forms part of a magnet assembly 34 that also includes a polarizing magnet 36 and RF coil 38.

In the example embodiment, RF system 30 includes an RF transmitter for producing RF pulses used in MR pulse sequences. The RF transmitter is responsive to the scan prescription and direction from pulse sequence server 20 to produce RF pulses of a desired frequency, phase, and pulse amplitude waveform. The generated RF pulses may be applied to RF coil 38 by RF system 30. Responsive MR signals detected by RF coil 38 are received by RF system 30, amplified, demodulated, filtered, and digitized under direction of commands produced by pulse sequence server 20. RF coil 38 is described as a transmit and receive coil such that RF coil 38 transmits RF pulses and detects MR signals. In one embodiment, MRI system 10 may include a transmit RF coil that transmits RF pulses and a separate receive coil that detects MR signals. A transmission channel of RF system 30 may be connected to a RF transmission coil and a receiver channel may be connected to a separate RF receive coil. Often, the transmission channel is connected to the whole body RF coil 38 and each receiver section is connected to a separate local RF coil.

In the example embodiment, RF system 30 also includes one or more RF receiver channels. Each RF receiver channel includes an RF amplifier that amplifies the MR signal received by RF coil 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M = \sqrt{I^2 + Q^2}; \tag{1}$$

and the phase of the received MR signal may also be determined as in Eq. (2) below:

$$\varphi = \tan^{-1}\left(\frac{Q}{I}\right). \tag{2}$$

In the example embodiment, the digitized MR signal samples produced by RF system 30 are received by data acquisition server 22. Data acquisition server 22 may operate in response to instructions downloaded from workstation 12 to receive real-time MR data and provide buffer storage such that no data is lost by data overrun. In some scans, data acquisition server 22 does little more than pass the acquired MR data to data processing server 24. In scans that need information derived from acquired MR data to control further performance of the scan, however, data acquisition server 22 is programmed to produce the needed information and convey it to pulse sequence server 20. For example, during prescans, MR data is acquired and used to calibrate the pulse sequence performed by pulse sequence server 20.

Also, navigator signals may be acquired during a scan and used to adjust the operating parameters of RF system 30 or gradient system 28, or to control the view order in which k-space is sampled.

In the example embodiment, data processing server 24 receives MR data from data acquisition server 22 and processes it in accordance with instructions downloaded from workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the example embodiment, images reconstructed by data processing server 24 are conveyed back to, and stored at, workstation 12. In some embodiments, real-time images are stored in a database memory cache (not shown in FIG. 1), from which they may be output to operator display 14 or a display 46 that is located near magnet assembly 34 for use by attending physicians. Batch mode images or selected real time images may be stored in a host database on disc storage 48 or on a cloud. When such images have been reconstructed and transferred to storage, data processing server 24 notifies data store server 26. Workstation 12 may be used by an operator to archive the images, produce films, or send the images via a network to other facilities.

In the example embodiment, MR system 10 includes an concomitant field correction computing device 102. Methods described herein may be implemented on concomitant field correction computing device 102. Concomitant field correction computing device 102 may include workstation 12 or may be included in workstation 12. Concomitant field correction computing device 102 may be included in MR system 10, or may be included in a separate computing device that is in communication with MR system 10, through wired or wireless communication. In some embodiments, concomitant field correction computing device 102 is a computing device separate from MR system 10 and receives data acquired by MR system 10 through a portable storage device, such as a flash drive or a thumb drive. In one example, concomitant field correction computing device 102 is a server computing device, and may be cloud-based.

In MR, when the amplitude of gradients are increased or when the magnetic field strength decreases, effects of concomitant fields increase. Concomitant fields result from the principle that under Maxwell's equations, there cannot be magnetic monopoles ($\nabla \cdot \vec{B}=0$) or rotation in the field ($\nabla \times \vec{B}=0$) in current source-free space. Concomitant fields cause time and spatial varying phase variance for each sample point ($k_x$, $k_y$, $k_z$) in the k-space. Effects of lower orders of concomitant fields such as less than two may be corrected by applying correction gradient pulses (pre-emphasis of linear spatial magnetic field gradients) or RF modulation (correction for spatially invariant terms) in known methods of concomitant field correction. The known methods, however, do not correct concomitant field effects from higher-order such as second order or higher in 3D acquisitions. This is because second order concomitant field errors vary quadratically in spatial terms. In a 3D pulse sequence, a slab or volume is excited by an excitation pulse like in a 2D pulse sequence. However, unlike in a 2D pulse sequence, to separate different slices in the excited 3D volume, a phase is imparted on spins along the slice direction by a series of slice encoding gradient pulses such that the $k_z$ dimension is sampled along a Cartesian grid or a non-Cartesian trajectory.

In MR, a pulse sequence or a sequence is a sequence of RF pulses, gradient pulses, and data acquisition applied by MRI system 10 in acquiring MR signals. An order of a concomitant field is the order of spatial dependency of the concomitant field. For example, if the concomitant field is a linear function of a spatial location z, the concomitant field may be referred to as a first-order concomitant field. A second-order concomitant field may be approximated as:

$$B_{c,2nd} \cong \frac{G_z^2}{8B_0} \cdot x^2 + \frac{G_z^2}{8B_0} \cdot y^2 + \frac{(G_x^2 + G_y^2)}{2B_0} \cdot z^2 - \frac{G_x G_z}{2B_0} \cdot xz - \frac{G_y G_z}{2B_0} \cdot yz, \quad (3)$$

where $B_{c,2nd}$ is the second-order concomitant field, $G_x$, $G_y$, and $G_z$ are gradients applied in the x, y, or z directions respectively, x, y, and z are the spatial dimensions in the image space, and $B_0$ is the static magnetic field strength of MR system 10 such as 1.5 T or 3.0 T.

As shown in Eqn. (3), the concomitant field is inversely proportional to the field strength $B_0$. A direct solution to reduce errors from concomitant fields is to increase the field strength of magnet 36. This solution is infeasible because upgrading the field strength of an MR system, such as from 1.5 T to 3.0 T, would essentially be replacing the entire MR system and would be too expensive. Further, as shown in Eqn. (3), the concomitant field is a function of square of the gradient strength G in a pulse sequence. To reduce the effects of the concomitant fields in an MR system, a user may have to resort to not using the maximum gradient strength provided by the gradient coil assembly in a pulse sequence, failing to take full advantage of capability of the gradient hardware.

In known methods of correcting effects from second-order concomitant fields, corrections are only performed for MR signals acquired with a 2D sequence. The known methods do not present systematic correction of the effects from gradients in all three dimensions in a 3D sequence. Nor do the known methods consider the effects when asymmetric gradients are applied. As such, 3D acquisitions with non-cartesian trajectories are typically avoided due to second order or higher concomitant field effects.

In contrast, systems and methods described here provide correction of high-order concomitant field effects without modification to the hardware. The high-order concomitant field is computed as a spatial and temporal function. The systems and methods described herein may be applied to MR signals acquired via Cartesian and non-Cartesian sampling. In Cartesian k-space sampling, linear gradients are applied along the x, y, and/or z directions such that $k_x$, $k_y$, $k_z$ are sampled along the Cartesian grids in the k-space. In non-Cartesian k-space sampling, one or more directions among the x, y, and z directions are not sampled along the Cartesian grids, and instead along non-Cartesian trajectories in k-space. In the systems and methods described herein, the effects of high-order concomitant fields may be corrected by including the phase accumulation caused by the high-order concomitant fields in the acquired MR signals in reconstructing MR images. The phase accumulation or phases vary as functions of the spatial locations and time. The reconstruction time and computation load may be reduced by setting phases in a volumetric patch or a 3D patch to be the same in the patch. In some embodiments, the reconstruction time and computation load may be reduced by applying a Fourier transform to the data along a dimension in which a linear gradient is applied. The systems and methods described herein enable a user to fully use capability of the gradient coil assembly without compromising image quality.

In an ideal situation where effects from concomitant fields are not present, the MR signals $S(k_x, k_y, k_z)$ are Fourier transform of the image $\rho(x, y, z)$ as:

$$S(k_x, k_y, k_z) = \int\int\int \rho(x, y, z)e^{-i(k_x x + k_y y + k_z z)} dx dy dz. \quad (4)$$

An MR image $\rho(x, y, z)$ may be reconstructed by applying inverse Fourier transform to the MR signals $S(k_x, k_y, k_z)$ if the k-space is sampled along a Cartesian grid or applying inverse Fourier transform to MR signals $S(k_x, k_y, k_z)$ re-gridded to a Cartesian grid in the non-Cartesian sampling dimension. The definition of k is given is:

$$k(t) = \gamma \int G(t) dt. \quad (5)$$

The phase of spins is given as:

$$\phi(t) = \gamma \int_0^t B(t') dt'. \quad (6)$$

As such, concomitant field errors, given in Eqn. (3), generate additional and erroneous phase in Eqn. (6). The MR signals become:

$$S(k_x, k_y, k_z) = \int\int\int \rho(x, y, z)e^{-i(k_x x + k_y y + k_z z)} e^{i\phi_{c2}(t; x, y, z)} dx dy dz. \quad (7)$$

The signals $S(k_x, k_y, k_z)$ are corrupted with additional phase accumulation or phases from concomitant fields. The concomitant fields generate additional and erroneous magnetic fields that distorts the expected k-space values, leading to errors in the image reconstruction. Effects of high-order concomitant fields may be corrected in reconstructing MR images by subtracting phases $\phi_{c2}(t; x, y, z)$ caused by the high-order concomitant fields as:

$$\rho(x, y, z) \approx \frac{1}{(2\pi)^3} \int\int\int S(k_x, k_y, k_z)e^{i(k_x x + k_y y + k_z z)} e^{-i\phi_{c2}(t; x, y, z)} dk_x dk_y dk_z, \quad (8)$$

where $\phi_{c2}(t; x, y, z)$ is the phase accumulated from second-order concomitant fields and may be referred to as a second-order concomitant phase. In general, Eqn. (8) is only approximately true.

$\phi_{c2}(t; x, y, z)$ may be derived based on the gradient applied as:

$$\phi_{c2}(t; x, y, z) = \frac{\gamma z^2}{4\pi B_0} \int_0^t (G_y^2(t) + G_x^2(t)) dt + \frac{\gamma(x^2 + y^2)}{16\pi B_0} \int_0^t G_z^2(t) dt - \frac{\gamma}{4\pi B_0} \left[ xz \int_0^t G_x(t) G_z(t) dt + yz \int_0^t G_y(t) G_z(t) dt \right], \quad (9)$$

where $\gamma$ is the gyromagnetic ratio of a nucleus such as proton. As shown in Eqn. (9), the second-order concomitant phase is a function of time and spatial locations. In a typical phase-correction method, the phase error is constant in time. The phase error may be corrected by deriving a phase map and then multiplying the MR signals with the complex conjugate of the phase map. In contrast, the second-order concomitant phase varies in time even at a given location (x, y, z). The known method of correcting phase errors is thus infeasible in correcting effects from concomitant fields, especially for high-order concomitant fields.

In some embodiments, the cross-terms of xz and yz in Eqn. (9) may be disregarded when the Gz gradient is not played at the same time as the Gx and Gy gradients. The condition that the Gz gradient is not played at the same time as the Gx and Gy gradients are met in a 2D pulse sequence, where the Gz gradient is a slice selection gradient and applied before the imaging gradients Gx and Gy. The condition may be met in a 3D pulse sequence such as stacks of spirals, stacks of stars, or stacks of fast spin echo (FSE). The Gz gradient is the second phase-encoding or slice encoding gradient, and is applied before the Gx and Gy gradients. The 3D volume acquisition is a stack of 2D planar $k_x$-$k_y$ acquisitions with slice encoding ($k_z$) in the third direction. In true 3D pulse sequences where three gradients are applied at the same time, such as in a 3D spirals sequence, the cross-terms of xz and yz may not be ignored and need to be calculated for each spatial position and time.

Figure 2:
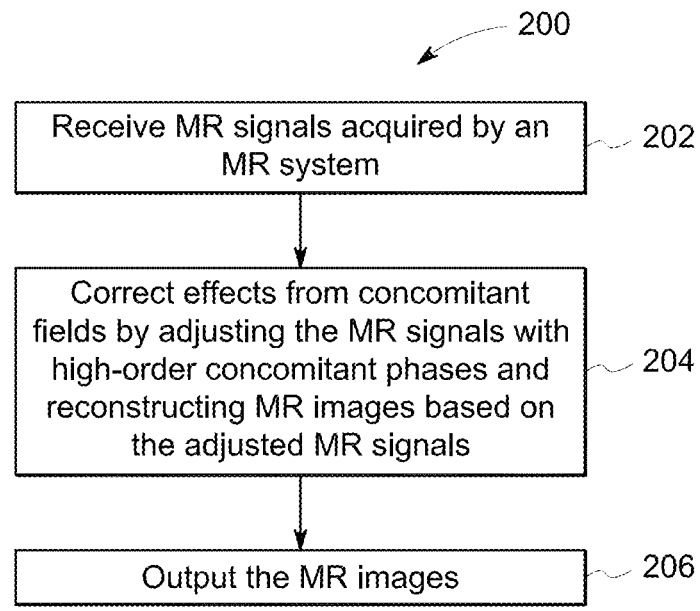
FIG. 2 is a flow chart of an example method of correcting effects of concomitant fields.

FIG. 2 is a flow chart of an example method 200 of correcting concomitant field effects. In the example embodiment, method 200 includes receiving 202 MR signals acquired with an MR system. The MR signals may be acquired by a 3D pulse sequence. Method 200 further includes correcting 204 effects from concomitant fields generated by gradient fields. Correcting 204 may include adjusting the MR signals with high-order concomitant phases accumulated from high-order concomitant fields. A high order is a second order or higher. For example, as shown in Eqn. (8), high-order concomitant phases are included in the reconstruction such that the MR signals are reconstructed with phases experienced from the application of gradients Gx, Gy, and/or Gz and the concomitant fields generated by the gradients. Effects of high-order concomitant fields need to be corrected because the effects become prominent due to the high-order dependence with the distance from the isocenter of the gradient assembly. For example, the second-order concomitant field is proportional to square of the distance from the gradient isocenter. Further, effects of second-order concomitant fields may not be corrected by modifications to gradients or RF modulation. High-order concomitant phases may be estimated. For example, second-order concomitant phases may be estimated using Eqn. (9). High-order concomitant phases may include phases from third order or higher, which may be derived based on high-order concomitant fields from Taylor series expansion of the magnetic field when gradients are applied. Alternatively, concomitant phases may be derived from concomitant fields measured or detected. A phase is proportional to a time integral of the magnetic field. Correcting 204 may further include reconstructing MR images based on the adjusted MR signals. In addition, method 200 includes outputting 206 the MR images.

In the example embodiment, the concomitant field effects are corrected for each (x, y, z) point in the image with a unique correction factor for that trajectory. The process is repeated for each (x, y, z) point. Special cases are for a stack of spirals or non-cartesian trajectory where the stack of planar slices acquisitions have in common with a blipped $k_z$ encoding. In stack of planar slices acquisitions, each slice is corrected by applying the correction phase for each slice, and then the inverse Fourier transform is performed to obtain an uncorrupted image for that slice. The data for the other slices are discarded. The process is repeated for the next slice, until all slices are corrected and reconstructed.

Figure 3A:
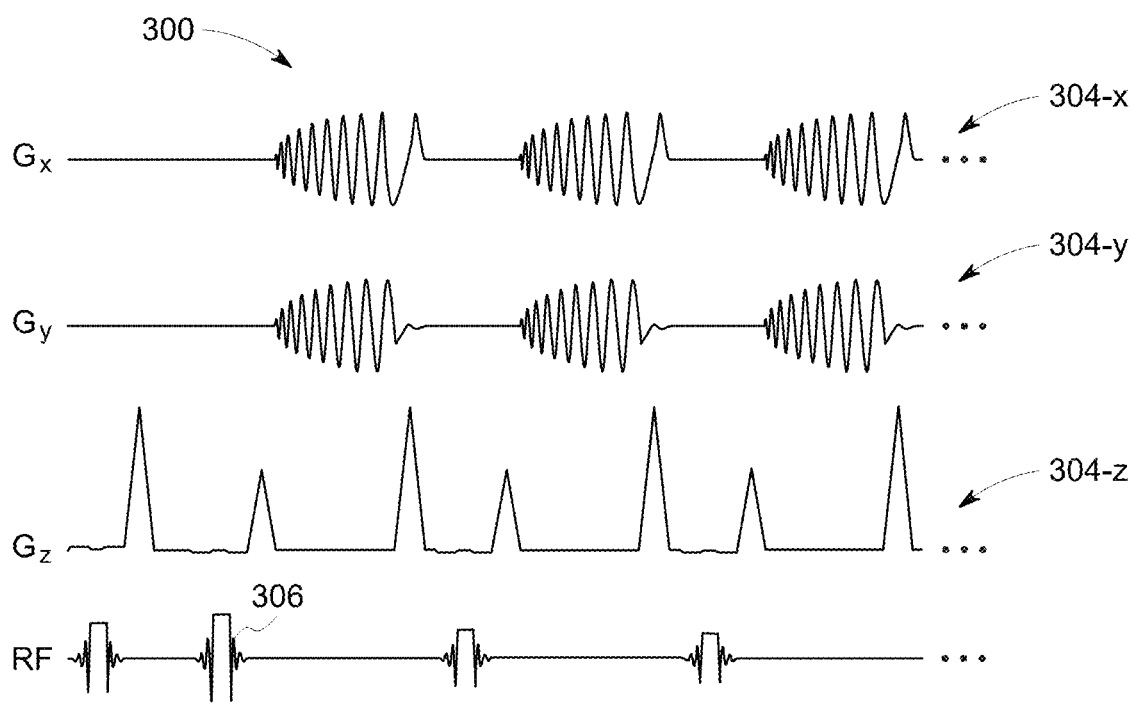
FIG. 3A is a schematic diagram of a 3D stacks of spirals sequence.
Figure 3B:
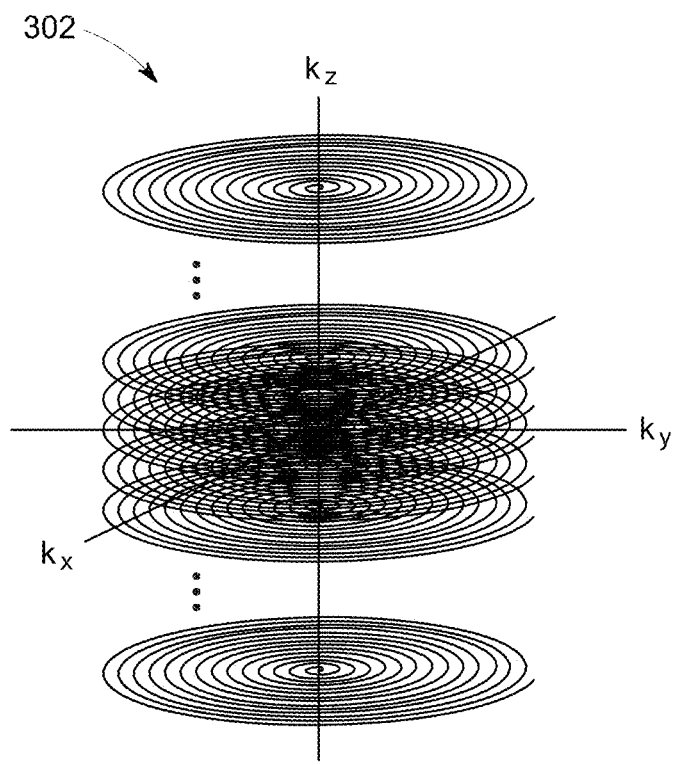
FIG. 3B is a schematic diagram of k-space trajectories of the pulse sequence shown in FIG. 3A.

FIG. 3A shows a sample pulse sequence 300 of 3D stacks of spirals. FIG. 3B shows k-space trajectories 302 when pulse sequence 300 is applied. $k_x(t)$, $k_y(t)$, and $k_z(t)$ at a given time is proportional to the integration of the gradient from time 0 to the time of t. In the example embodiment, pulse sequence 300 includes in-plane encoding gradients Gx 304-$x$ and Gy 304-$y$, and slice-encoding gradient Gz 304-$z$. A linear gradient is applied in slice-encoding gradient Gz 304-$z$ such that the $k_z$ dimension is sampled along a Cartesian grid. The slice-encoding gradient Gz defines a $k_z$ location in the k-space. Slice-encoding gradient Gz 304-$z$ is applied at the different time from Gx and Gy gradients 304-$x$, 304-$y$. The integrals of Gx and Gy gradients 304-$x$, 304-$y$, or $k_x$ and $k_y$, are in the shapes of spirals. As a result, the $k_x$-$k_y$ plane at the $k_z$ location is sampled in spiral trajectories, and the 3D k-space is sampled by stacks of spiral trajectories 302.

In the example embodiment, killer gradients or crusher gradients $G_k$ are provided at both sides of the 180° refocusing RF pulse 306 in the z direction (see FIG. 3A) to remove or reduce transverse coherence. The amplitude of each crusher gradient $G_k$ is chosen to be close to the maximum gradient $G_{max}$, to shorten the gradient pulse duration. Crusher gradients $G_k$ are of equal duration and amplitude, to ensure that the crusher gradients do not contribute to a net phase from concomitant field effects. The phase-encoding gradients $G_e$ may be referred to as blips or unipolar gradient waveforms. Phase-encoding gradients $G_e$ may be applied separately from the crusher gradient $G_k$. Because of a 180° refocusing RF pulse 306, the phase errors caused by concomitant fields generated by the crusher gradients on the left and right sides of refocusing RF pulse 306 cancel one another. The phase errors caused by concomitant fields generated by the separate phase-encoding and crusher z gradients are proportional to $G_e^2$. $G_e$ may be combined with the crusher gradient $G_k$ as one gradient pulse as shown in FIG. 3A. The phase errors caused by concomitant fields generated by the combined z gradients are proportional to $G_e^2 + 2G_eG_k$. The amplitudes and/or durations of the blips $G_e$ are small relative to $G_x$, $G_y$, and/or $G_k$ gradients. Terms $$\frac{G_z^2}{8B_0} \cdot x^2 \text{ and } \frac{G_z^2}{8B_0} \cdot y^2$$

in Eqn. (3) may approximate to zero and may be ignored when the crusher gradient $G_k$ is applied separately from the phase-encoding gradient $G_e$. In addition, Gx and Gy are not coincident or played at the same time as the $G_z$ gradient, and therefore cross terms $$\frac{G_xG_z}{2B_0} \cdot xz \text{ and } \frac{G_yG_z}{2B_0} \cdot yz$$

also approximate to zero and may be ignored.

As a result, the second-order of concomitant field in a 3D stacks of spirals sequence may be approximated as:

$$\phi_{c2}(z) = \zeta(t)z^2, \text{ where } \zeta(t) = \frac{\gamma}{2B_0} \cdot \int_0^t (G_x^2(t') + G_y^2(t'))dt'. \quad (10)$$

If $S'(k_x, k_y, z)$ denotes the Fourier transform of $S(k_y, k_y, k_z)$ along the $k_z$ dimension, $S'(k_x, k_y, z)$ may be written as:

$$S'(k_x, k_y, z) = \frac{1}{2\pi} \int \int U(k_x, k_y, z')e^{ik_z(z-z')}dk_z dz' = \quad (11)$$

$$\int U(k_x, k_y, z')\delta(z-z')dz' = U(k_x, k_y, z),$$

where $$\delta(z-z') = \frac{1}{2\pi}\int e^{ik_z(z-z')}dk_z$$

is the Dirac delta function, and $$U(k_x, k_y, z) = \int\int \rho(x, y, z)e^{-i(k_xx+k_yy)}dxdy. \quad (12)$$

$U(k_x, k_y, z)$ is the 2D Fourier transform of the image p at a given slice position z. $S'(k_x, k_y, z)$ may be referred to as $k_z$-transformed data.

Accordingly, when the image is contaminated by $\phi_{c2}(z)$ as $\rho$ becomes $\rho e^{i\phi_{c2}(z)}$, $$S'(k_x, k_y, z) = \int\int U(k_x, k_y, z')\delta(z-z')e^{i\zeta z^2}dz', \quad (13)$$

which indicates that for each z' location, there is a different phase contribution. This contributes to greater blurring as distance increases, where z increases further from the isocenter. In reconstruction, the exponential term comes out the integral over x and y in U, and the image may be reconstructed by:

$$\rho(x, y, z) = \frac{1}{(2\pi)^2} \int\int S'(k_x, k_y, z)e^{-i\zeta z^2}e^{i(k_xx+k_yy)}dk_x dk_y. \quad (14)$$

If $\zeta \to 0$, Eqn. (14) reconstructs the image $\rho(x, y, z)$ exactly. However, if $\zeta \neq 0$, Eqn. (14) indicates that a phase correction applied to each slice location will result in an unblurred image but only for that particular slice location as:

$$S''(k_x, k_y, z) = \frac{1}{2\pi}\int U(k_x, k_y, z')\delta(z-z')e^{i\zeta z^2}e^{-i\zeta z'^2}dz', \quad (15)$$

to negate the effect of the concomitant field.

Eqn. (15) is a special case of Eqn. (7), and represents the corrected image for 3D acquisition where the $k_z$ dimension is sampled along a Cartesian grid. A reconstruction of 3D MR signals becomes a 2D operation in Eqn. (15) along $k_x$ and $k_y$, with additional phases $\zeta(t)z^2$. For given $k_x$ and $k_y$ trajectories, the additional phases $\zeta(t)z^2$ at the given time t corresponding to $k_x(t)$ and $k_y(t)$ may be calculated. Methods such as re-gridding or non-uniform Fourier transform may be used to reconstruct the 3D images $\rho(x, y, z)$ correcting for $\zeta(t)z^2$ for each point in time t and slice position z.

A 3D stacks of spirals sequence is described as an example for illustration purposes only. Systems and methods described herein may be applied to other 3D stack of planar slices acquisitions. In 3D stack of planar slices acquisitions, the $k_z$ dimension is sampled along a Cartesian grid, such as 3D stacks of stars, 3D propeller where each $k_x$-$k_y$ plane is sampled with a propeller sampling pattern, 3D echo-planar imaging (EPI), or 3D FSE.

Figure 4:
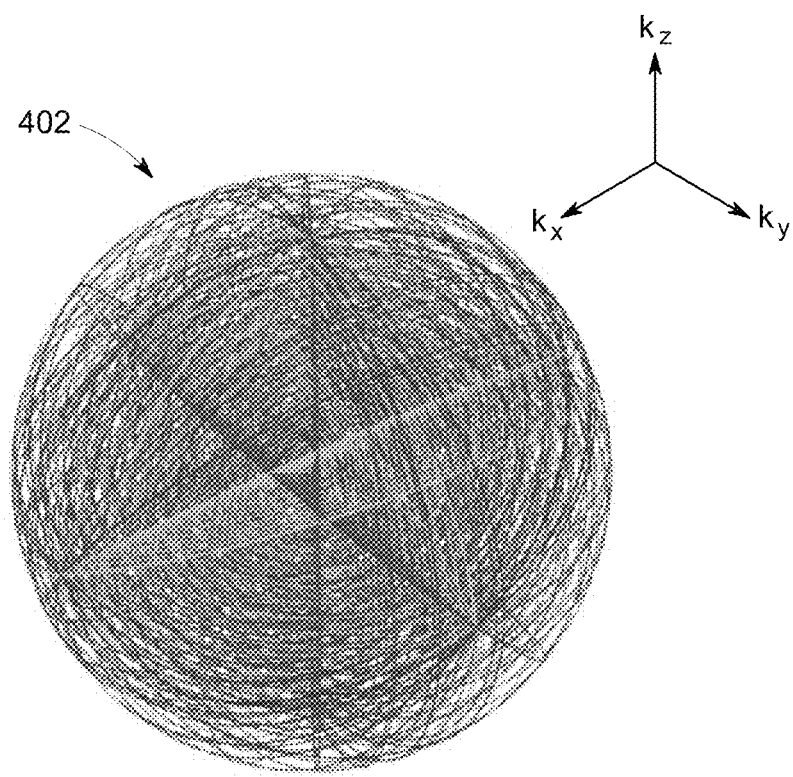
FIG. 4 shows k-space trajectories of a 3D spirals sequence.

FIG. 4 is a schematic diagram of trajectories 402 of a 3D spirals sequence. Unlike 3D stacks of spirals sequence 300, where the $k_z$ dimension is phase-encoded by a blip, a 3D spiral sequence includes a $G_z$ gradient that has a trajectory of a spiral in the $k_z$ dimension. Trajectories 402 include spirals spiraling in the 3D k-space. Instead of blips in stacks of spirals sequence 300, the $G_z$ gradient is played at the same time as the $G_x$ and $G_y$ gradients. As a result, the $k_z$ dimension may not be separated out in Eqn. (8) and the reconstruction may not be simplified to a 2D reconstruction at a plurality of z locations. As such the concomitant phase varies with each time point in the $k_x(t)$-$k_y(t)$-$k_z(t)$ trajectory.

In Eqn. (8), to reconstruct the image $\rho(x, y, z)$ at image location (x, y, z), the k-space data or the MR signals are corrected with phases $\phi_{c2}(t; x, y, z)$ accumulated from the second-order concomitant field at all $k_x$, $k_y$, and $k_z$ locations. Phases $\phi_{c2}(t; x, y, z)$ temporally vary as a function of time t that corresponds to the k-space location ($k_x$, $k_y$, $k_z$). Phases $\phi_{c2}(t; x, y, z)$ also spatially vary as a function of x, y, and z. The variables t, x, y, and/or z often are not separable, in which case Eqn. (8) may need to be calculated for individual voxels, resulting in a formidable computation load. As in the case of the stack-of-spirals example, for a non-cartesian 3D k-space trajectory, the image $\rho(x, y, z)$ at image location (x, y, z), the k-space data or the MR signals are corrected with phases $\phi_{c2}(t; x, y, z)$ and the data for that location (x, y, z) retained, with data for other voxels discarded. The next image location (x', y', z') is then reconstructed with the corrected phases $\phi_{c2}(t; x', y', z')$ and the data for that location (x', y', z') retained, with the process repeated for all (x, y, z) locations. Hence, the formidable computational load is faced in the reconstruction.

Figure 5:
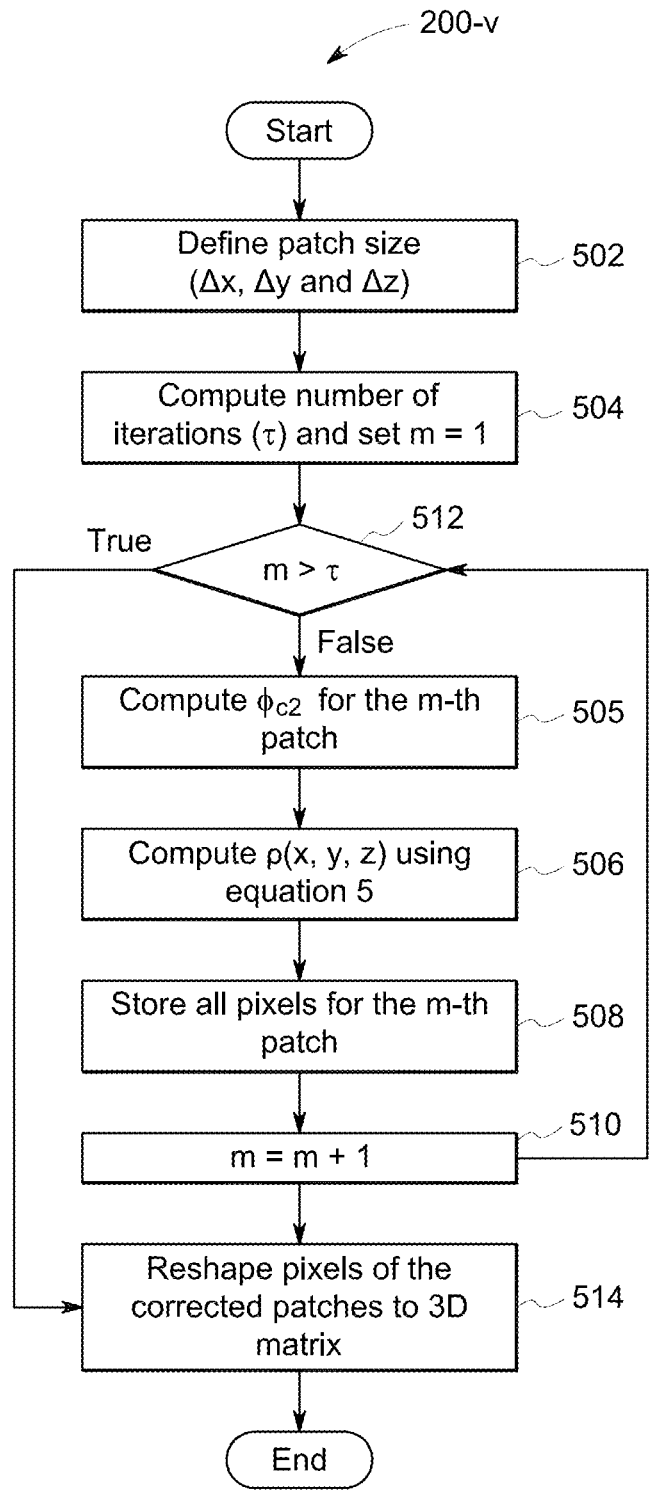
FIG. 5 is a flow chart of an example embodiment of a method of correcting effects of concomitant fields.

FIG. 5 is a flow chart of an example embodiment of method 200-v, where a volumetric patch-based method is used to reduce the computation load in reconstruction. In the example embodiment, method 200-v includes determining 502 a patch size ($\Delta x$, $\Delta y$, $\Delta z$). The patch size may be determined by limiting phase variations from the concomitant field effects in the patch to be below a threshold level. For example, the threshold level may be set as a phase corresponding to a concomitant field dispersion, or the frequency dispersion, at 0.5 ppm (approximately 65 Hz for 3 T) because a frequency/field variation of 0.5 ppm or more often leads to blurring in the reconstructed image in a non-Cartesian acquisition. The threshold level may be set as a phase corresponding to a field dispersion of less than 0.5 ppm to improve the quality of the reconstructed images. Method 200-v includes computing 504 the number of iterations ($\tau$). $\tau$ may be calculated as:

$$\tau = \frac{n_x n_y n_z}{\Delta x \Delta y \Delta z}, \quad (16)$$

where $n_x$, $n_y$, and $n_z$ are numbers of pixels in the x, y, z directions respectively, while $\Delta x$, $\Delta y$, and $\Delta z$ are numbers of pixels in the patch in the x, y, z directions respectively. Selection of the patch size is a trade-off between image quality and computation load. The smaller the patch size, the image quality of the reconstructed image may increase with the cost of increased computation load and reconstruction time.

In the example embodiment, a patch counter m is first set to 1. If m is less than the number of iterations, method 200-v includes computing 505 a phase $\phi_{c2}(t; x, y, z)$ from the second-order concomitant field for the m-th patch. The phase may be calculated according to Eqn. (9). Only one phase of the phases in the patch is calculated using any location (x, y, z) in the patch. Method 200-v further includes computing or reconstructing 506 the image $\rho(x, y, z)$ at pixel (x, y, z) based on Eqn. (8). Reconstructing 506 may include re-gridding to a Cartesian grid. Alternatively, reconstructing 506 may include applying a non-uniform Fourier transform. Computing 506 the image $\rho(x, y, z)$ is repeated for pixels in patch m, using the same phase $\phi_{c2}$ for the patch. Image $\rho(x, y, z)$ at pixels in the m-th patch is stored 508. Patch counter m is increased 510 by 1 such that the reconstruction proceeds to the next patch. Method 200-v loops back to checking 512 whether patch counter m is greater than the number of iterations. If patch counter m is less than the number of iterations, computing 505 $\phi_{c2}(t; x, y, z)$, reconstructing 506, and storing 508 are performed for the patch. The process is repeated for all patches.

In the example embodiment, when patch counter m is greater than the number of iterations, the reconstruction of the 3D volume is completed and method 200-v may further include reshaping 514 pixels of the corrected patches to a 3D matrix. The reshaping is carried out to re-dimension the corrected patches to yield a 3D image that has the same dimension as the uncorrected/corrupted image. Reshaping is needed because in each iteration, all other patches have been discarded except for the corrected patch. The corrected patches need to be put in their appropriate locations to form the 3D corrected image.

A 3D spirals sequence is described herein as an example for illustration purposes. Systems and method described herein may be used to increase reconstruction speed while correcting concomitant field effects in any pulse sequences, especially for a 3D pulse sequence in which the $k_x$, $k_y$, and $k_z$ dimensions are sampled along a non-Cartesian trajectory.

Figure 6:
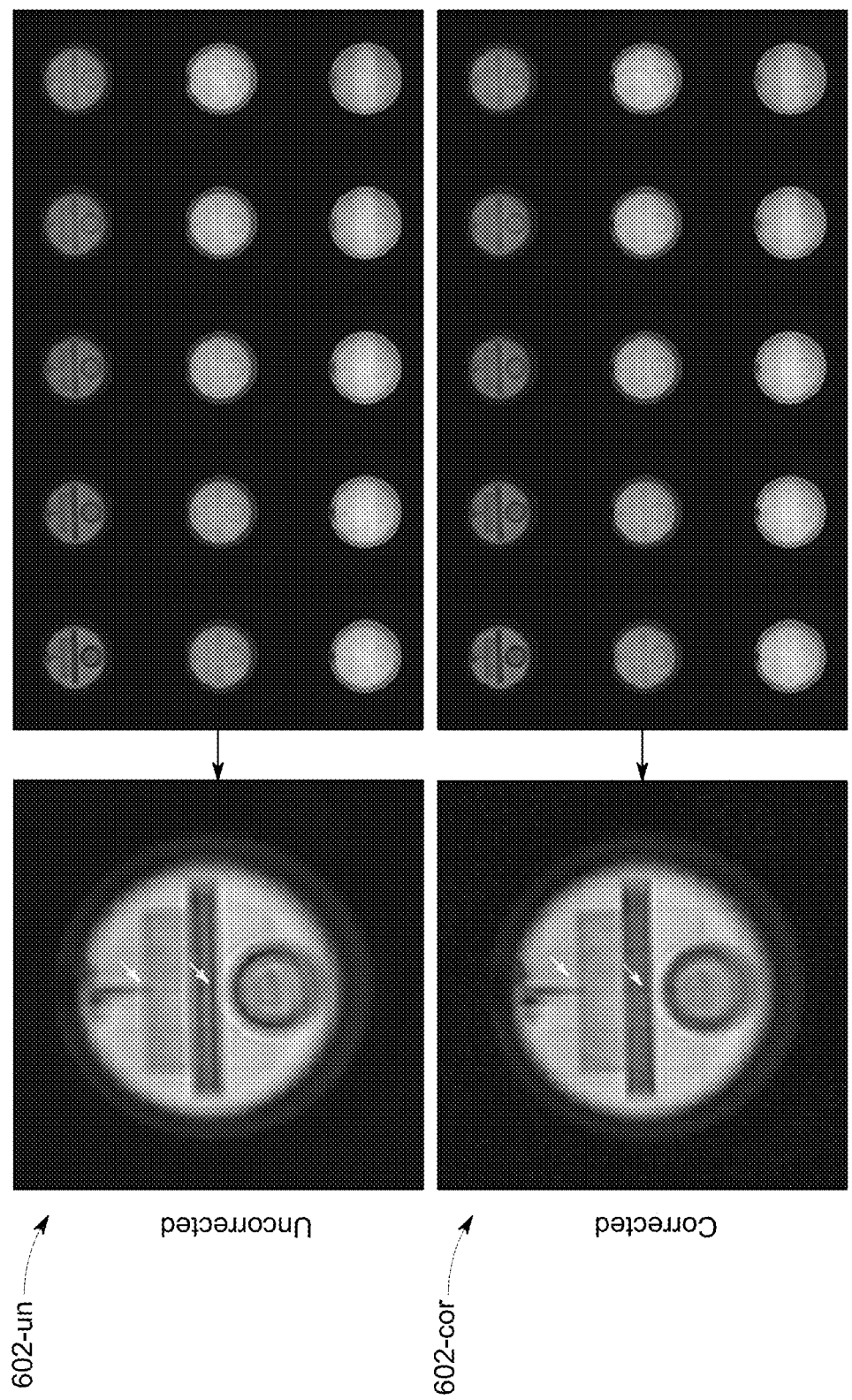
FIG. 6 shows images with and without correction of the effects of concomitant fields using the method shown in FIG. 2.

FIG. 6 shows that in-plane and through-plane blurring caused by second-order concomitant phase errors is corrected using the systems and methods described herein. The images are acquired using a 3D stacks of spirals FSE sequence. Images 602-un of the top row are not corrected. Images 602-cor of the bottom row are corrected using the systems and methods described herein. In image 602-cor, the edges are sharper and the signal uniformity is greater than uncorrected image 602-un (see areas marked by white arrows).

Figure 7A:
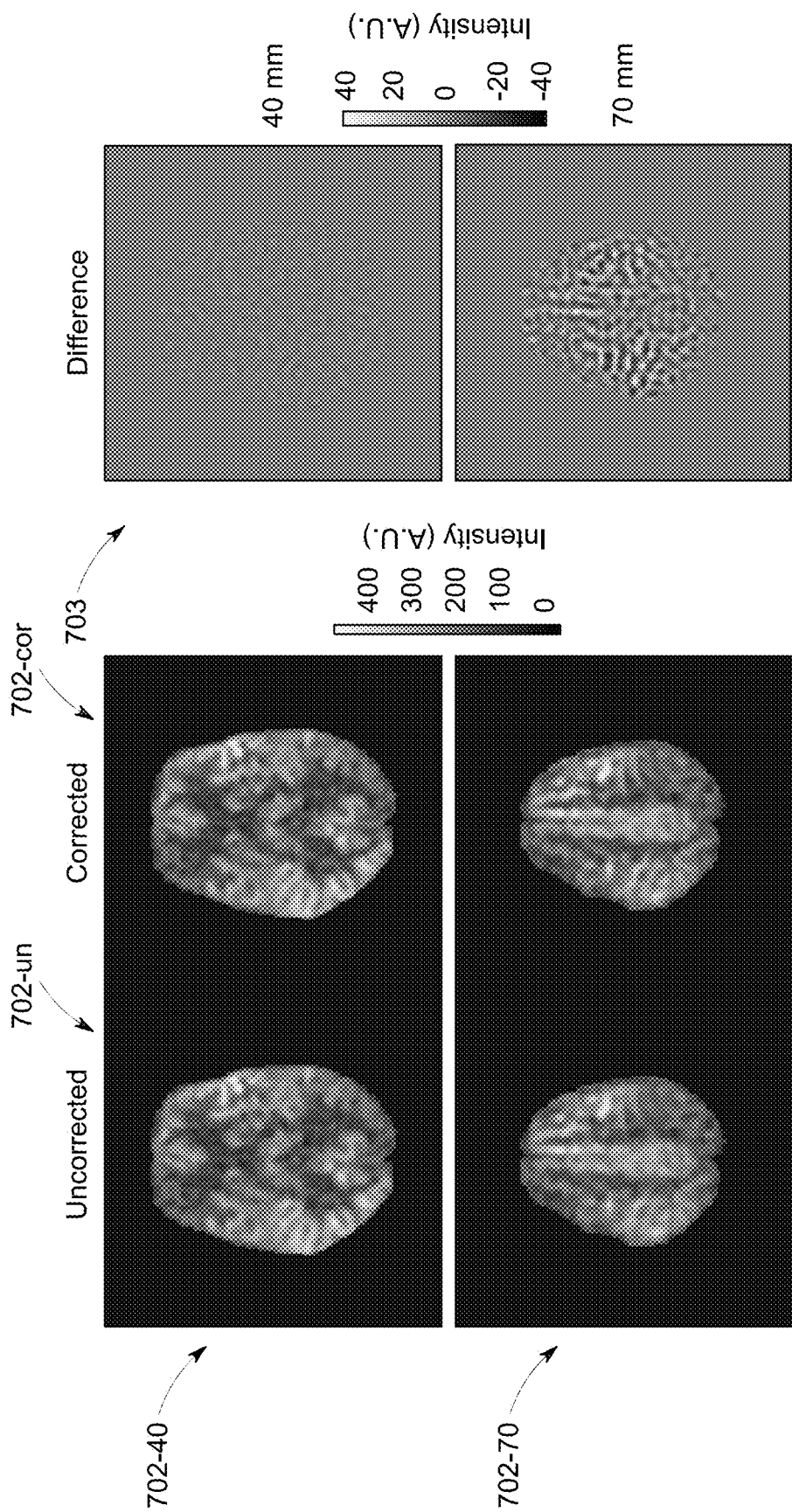
FIG. 7A shows perfusion-weighted images with and without correction of the effects of concomitant fields using the method shown in FIG. 2.
Figure 7B:
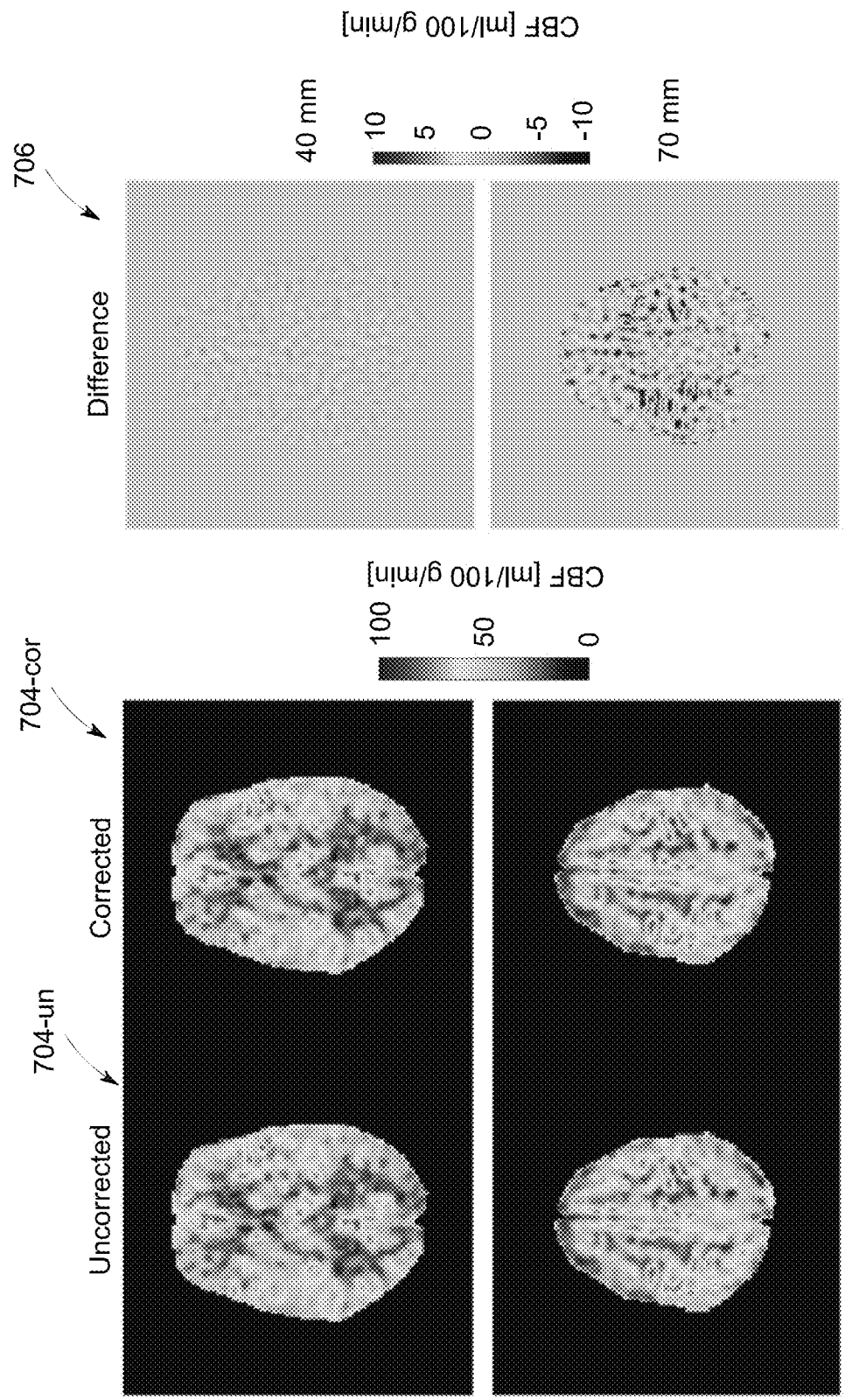
FIG. 7B shows cerebral blood flow (CBF) maps generated with the perfusion-weighted images with and without correction of the effects of concomitant fields using the method shown in FIG. 2.

FIGS. 7A and 7B show that systems and methods described herein are used to increase accuracies of perfusion studies. FIG. 7A shows perfusion-weighted images 702 and differences 703 between corrected and uncorrected images 702. FIG. 7B shows cerebral blood flow (CBF) maps 704 obtained based on the perfusion-weighted images and differences 706 between corrected and uncorrected CBF maps 704. The perfusion-weighted images are acquired by 3D pCASL (pseudo-continuous arterial spin labeling) and a 3D stacks of spirals FSE sequence in the image acquisition. Images 702-40 and 702-70 are perfusion-weighted axial images at 40 mm or 80 mm from the isocenter of the gradients, respectively. Images 702-un in the left column are not corrected for second-order concomitant field effects, while images 702-cor in the middle column are corrected for second-order concomitant field effects. The right column shows the difference images 703 between corrected images 702-cor and uncorrected images 702-un. The differences in images 702-70 at 70 mm are greater than the differences in the images 702-40 at 40 mm. Similarly, the differences between corrected and uncorrected CBF maps 704 are greater at 70 mm than at 40 mm. At locations farther away from the isocenter of the gradient coil assembly, the effects of high-order concomitant field are greater due to the high order dependence with the distance. As a result, due to concomitant field effects, artifacts and errors in images and functional maps such as CBF maps increase as the imaging location is further away from the isocenter of the gradient coil assembly. Without correction of high-order concomitant field effects, errors in the images and functional maps would compromise diagnosis.

Figure 8:
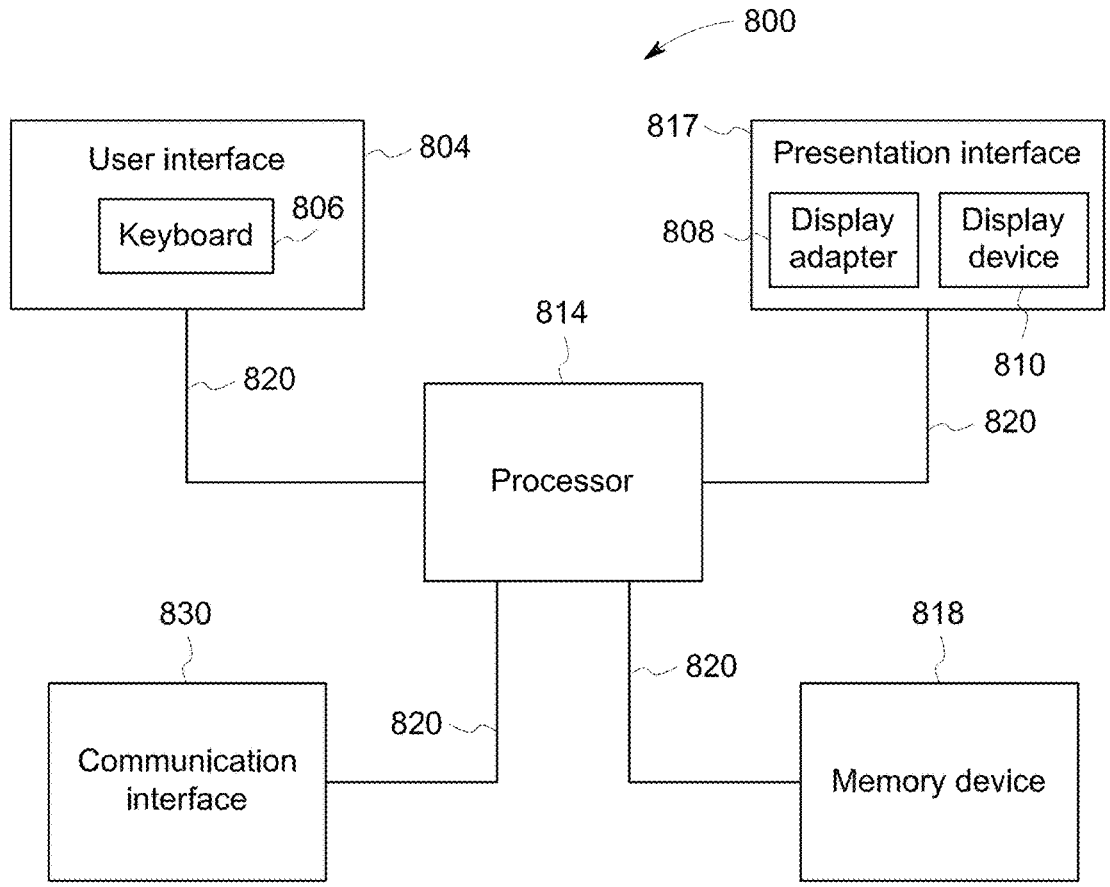
FIG. 8 is a block diagram of an example computing device.

Workstation 12 and concomitant field correction computing device 102 described herein may be any suitable computing device 800 and software implemented therein. FIG. 8 is a block diagram of an example computing device 800. In the example embodiment, computing device 800 includes a user interface 804 that receives at least one input from a user. User interface 804 may include a keyboard 806 that enables the user to input pertinent information. User interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the example embodiment, computing device 800 includes a presentation interface 817 that presents information, such as input events and/or validation results, to the user. Presentation interface 817 may also include a display adapter 808 that is coupled to at least one display device 810. More specifically, in the example embodiment, display device 810 may be a visual display device, such as a cathode ray tube (CRT), a liquid crystal display (LCD), a light-emitting diode (LED) display, and/or an "electronic ink" display. Alternatively, presentation interface 817 may include an audio output device (e.g., an audio adapter and/or a speaker) and/or a printer.

Computing device 800 also includes a processor 814 and a memory device 818. Processor 814 is coupled to user interface 804, presentation interface 817, and memory device 818 via a system bus 820. In the example embodiment, processor 814 communicates with the user, such as by prompting the user via presentation interface 817 and/or by receiving user inputs via user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are example only, and thus are not intended to limit in any way the definition and/or meaning of the term "processor."

In the example embodiment, memory device 818 includes one or more devices that enable information, such as executable instructions and/or other data, to be stored and retrieved. Moreover, memory device 818 includes one or more computer readable media, such as, without limitation, dynamic random access memory (DRAM), static random access memory (SRAM), a solid state disk, and/or a hard disk. In the example embodiment, memory device 818 stores, without limitation, application source code, application object code, configuration data, additional input events, application states, assertion statements, validation results, and/or any other type of data. Computing device 800, in the example embodiment, may also include a communication interface 830 that is coupled to processor 814 via system bus 820. Moreover, communication interface 830 is communicatively coupled to data acquisition devices.

In the example embodiment, processor 814 may be programmed by encoding an operation using one or more executable instructions and providing the executable instructions in memory device 818. In the example embodiment, processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Figure 9:
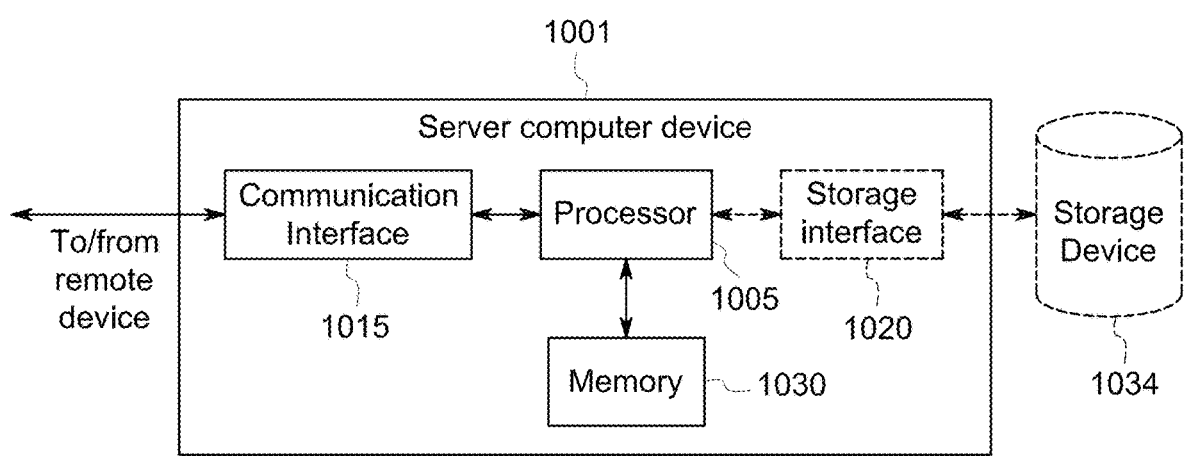
FIG. 9 is a block diagram of an example server computing device.

FIG. 9 illustrates an example configuration of a server computer device 1001 such as computing device 102. Server computer device 1001 also includes a processor 1005 for executing instructions. Instructions may be stored in a memory area 1030, for example. Processor 1005 may include one or more processing units (e.g., in a multi-core configuration).

Processor 1005 is operatively coupled to a communication interface 1015 such that server computer device 1001 is capable of communicating with a remote device or another server computer device 1001. For example, communication interface 1015 may receive data from workstation 12, via the Internet.

Processor 1005 may also be operatively coupled to a storage device 1034. Storage device 1034 is any computer-operated hardware suitable for storing and/or retrieving data. In some embodiments, storage device 1034 is integrated in server computer device 1001. For example, server computer device 1001 may include one or more hard disk drives as storage device 1034. In other embodiments, storage device 1034 is external to server computer device 1001 and may be accessed by a plurality of server computer devices 1001. For example, storage device 1034 may include multiple storage units such as hard disks and/or solid state disks in a redundant array of independent disks (RAID) configuration. storage device 1034 may include a storage area network (SAN) and/or a network attached storage (NAS) system.

In some embodiments, processor 1005 is operatively coupled to storage device 1034 via a storage interface 1020. Storage interface 1020 is any component capable of providing processor 1005 with access to storage device 1034. Storage interface 1020 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 1005 with access to storage device 1034.

At least one technical effect of the systems and methods described herein includes (a) correcting high-order concomitant field effects; (b) increasing reconstruction speed by Fourier transforming along a Cartesian-sampling dimension before correcting high-order concomitant field effects; and (c) increasing reconstruction speed using volumetric patches.

Example embodiments of systems and methods of correcting concomitant field effects are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A magnetic resonance (MR) system, comprising:
a gradient coil assembly comprising an x gradient coil, a y gradient coil, and a z gradient coil, wherein the x gradient coil, the y gradient coil, or the z gradient coil is configured to apply a gradient field along an x direction (Gx), a gradient field along a y direction (Gy), or a gradient field along a z direction (Gz), respectively; and
a concomitant field correction computing device, comprising at least one processor in communication with at least one memory device, and the at least one processor programmed to:
receive MR signals acquired with the MR system using a three-dimensional (3D) pulse sequence, wherein a $k_x$ dimension and a $k_y$ dimension in k-space are sampled along non-Cartesian trajectories;
correct effects of concomitant fields generated by gradient fields applied by the gradient coil assembly by:
adjusting the MR signals with second-order concomitant phases accumulated from second-order concomitant fields, wherein the second-order concomitant phases vary as functions of time and spatial locations; and
reconstructing MR images based on the adjusted MR signals; and
output the MR images.

2. The MR system of claim 1, wherein the at least one processor is further programmed to:
receive the MR signals acquired by sampling in a $k_z$ dimension along a Cartesian grid; and
correct the effects of the concomitant fields by:
applying a Fourier transform to the MR signals along the $k_z$ dimension to derive $k_z$-transformed data;
for each z location in a z dimension, correcting the effects of the concomitant fields by:
adjusting the MR signals with the second-order concomitant phases, wherein the second-order concomitant phases are functions of $z^2$; and
reconstructing along a $k_x$-$k_y$ plane at the z location to derive an x-y image at the z location.

3. The MR system of claim 2, wherein the second-order concomitant phases are proportional to $z^2$ with a factor being proportional to time integrals of $G_x^2$ and $G_y^2$.

4. The MR system of claim 1, wherein the at least one processor is further programmed to:
receive the MR signals acquired by sampling in a $k_z$ dimension along a non-Cartesian trajectory; and
determine a patch size of a volumetric patch, wherein phase variations from the effects of the concomitant fields at pixels in the volumetric patch are less than a threshold.

5. The MR system of claim 4, wherein for each volumetric patch, the at least one processor is further programmed to:
compute one of the second-order concomitant phases corresponding to one of pixels in the volumetric patch;
set the second-order concomitant phases in the volumetric patch to the one of the second-order concomitant phases; and
reconstructing the MR images at the pixels in the volumetric patch based on the set second-order concomitant phase.

6. The MR system of claim 4, wherein the threshold is set as a phase corresponding to a concomitant field dispersion of 0.5 ppm.

7. A concomitant field correction computing device for correcting effects of concomitant fields in a magnetic resonance (MR) system, comprising at least one processor in communication with at least one memory device, and the at least one processor programmed to:
receive MR signals acquired with an MR system using a three-dimensional (3D) pulse sequence, wherein the MR system includes:
a gradient coil assembly including an x gradient coil, a y gradient coil, and a z gradient coil, wherein the x gradient coil, the y gradient coil, or the z gradient coil is configured to apply a gradient field along an x direction (Gx), a gradient field along a y direction (Gy), or a gradient field along a z direction (Gz), respectively; and
correct effects of concomitant fields generated by gradient fields applied by the gradient coil assembly by:
adjusting the MR signals with second-order concomitant phases accumulated from second-order concomitant fields, wherein the second-order concomitant phases vary as functions of time and spatial locations; and
reconstructing MR images based on the adjusted MR signals; and
output the MR images.

8. The computing device of claim 7, wherein the at least one processor is further programmed to:
receive the MR signals acquired by sampling in a $k_z$ dimension along a Cartesian grid; and
correct the effects of the concomitant fields by:
applying a Fourier transform to the MR signals along the $k_z$ dimension to derive $k_z$-transformed data;
for each z location in a z dimension, correcting the effects of the concomitant fields by:

adjusting the MR signals with the second-order concomitant phases, wherein the second-order concomitant phases are functions of $z^2$; and reconstructing along a $k_x$-$k_y$ plane at the z location to derive an x-y image at the z location.

9. The computing device of claim 8, wherein the second-order concomitant phases are proportional to $z^2$ with a factor being proportional to time integrals of $G_x^2$ and $G_y^2$.

10. The computing device of claim 7, wherein the at least one processor is further programmed to:

receive the MR signals acquired by sampling in a $k_z$ dimension along a non-Cartesian trajectory; and determine a patch size of a volumetric patch, wherein phase variations from the effects of the concomitant fields at pixels in the volumetric patch are less than a threshold.

11. The computing device of claim 10, wherein for each volumetric patch, the at least one processor is further programmed to:

compute one of the second-order concomitant phases corresponding to one of pixels in the volumetric patch;

set the second-order concomitant phases in the volumetric patch to the one of the second-order concomitant phases; and reconstructing the MR images at the pixels in the volumetric patch based on the set second-order concomitant phase.

12. The computing device of claim 10, wherein the threshold is set as a phase corresponding to a concomitant field dispersion of 0.5 ppm.

13. A method for correcting effects of concomitant fields in a magnetic resonance (MR) system, the method comprising:

receiving MR signals acquired with an MR system using a three-dimensional (3D) pulse sequence, wherein the MR system includes:

a gradient coil assembly including an x gradient coil, a y gradient coil, and a z gradient coil, wherein the x gradient coil, the y gradient coil, or the z gradient coil is configured to apply a gradient field along an x direction (Gx), a gradient field along a y direction (Gy), or a gradient field along a z direction (Gz), respectively; and correcting effects of concomitant fields generated by gradient fields applied by the gradient coil assembly by:

adjusting the MR signals with high-order concomitant phases accumulated from high-order concomitant fields, wherein the high-order concomitant phases vary as functions of time and spatial locations, and a high order is a second order or higher; and reconstructing MR images based on the adjusted MR signals; and outputting the MR images.

14. The method of claim 13, wherein:

receiving MR signals further comprises receiving the MR signals acquired by sampling in a $k_z$ dimension along a Cartesian grid; and correcting effects further comprises correcting the effects of the concomitant fields by:

applying a Fourier transform to the MR signals along the $k_z$ dimension to derive $k_z$-transformed data;

for each z location in a z dimension, correcting the effects of the concomitant fields by:

adjusting the MR signals with the high-order concomitant phases, wherein the high-order concomitant phases are functions of $z^2$; and reconstructing along a $k_x$-$k_y$ plane at the z location to derive an x-y image at the z location.

15. The method of claim 14, wherein the high-order concomitant phases are proportional to $z^2$ with a factor being proportional to time integrals of $G_x^2$ and $G_y^2$.

16. The method of claim 13, wherein:

receiving MR signals further comprises receiving the MR signals acquired by sampling in a $k_z$ dimension along a non-Cartesian trajectory; and the method further comprises determining a patch size of a volumetric patch, wherein phase variations from the effects of the concomitant fields at pixels in the volumetric patch are less than a threshold.

17. The method of claim 16, wherein for each volumetric patch, correcting effects further comprises:

computing one of the high-order concomitant phases corresponding to one of pixels in the volumetric patch;

setting the high-order concomitant phases in the volumetric patch to the one of the high-order concomitant phases; and reconstructing the MR images at the pixels in the volumetric patch based on the set high-order concomitant phase.

18. The method of claim 16, wherein the threshold is set as a phase corresponding to a concomitant field dispersion of 0.5 ppm.

19. The method of claim 16, wherein the threshold is set as a phase corresponding to a field dispersion of less than 0.5 ppm to improve quality of reconstructed images.

* * * * *